| United States Patent [19] | [11] Patent Number: 4,792,522 |
| Nettleton, Jr. et al. | [45] Date of Patent: Dec. 20, 1988 |

[54] RIGOLETTONE ANTITUMOR COMPLEX

[75] Inventors: Donald E. Nettleton, Jr., Jordon; Stanley W. Bray, East Syracuse; James A. Bush, Fayetteville; William T. Bradner, Manlius, all of N.Y.

[73] Assignee: Bristol-Myers Company, New York, N.Y.

[21] Appl. No.: 768,389

[22] Filed: Aug. 22, 1985

Related U.S. Application Data

[63] Continuation of Ser. No. 560,772, Dec. 12, 1983, abandoned, which is a continuation-in-part of Ser. No. 517,866, Jul. 27, 1983, abandoned.

[51] Int. Cl.$^4$ .................. C12P 23/00; C12N 1/20; A61K 35/00
[52] U.S. Cl. .................. 435/67; 435/172.1; 435/886; 424/115; 424/122; 424/124; 549/294
[58] Field of Search .................. 435/67, 68, 70, 886, 435/253, 172.1; 424/115, 122, 124; 549/294

[56] References Cited

U.S. PATENT DOCUMENTS

| | | | |
|---|---|---|---|
| 4,202,886 | 5/1980 | Ohba et al. | 424/122 |
| 4,283,390 | 8/1981 | Koch et al. | 424/122 |
| 4,548,814 | 10/1985 | Rinehurts Jr. | 424/95 |

FOREIGN PATENT DOCUMENTS 55-118499  9/1980  Japan .................. 435/67

OTHER PUBLICATIONS

Hamamoto et al. *J Antibiotics*, vol. XXXVI, No. 6, Jun. 1983, pp. 639-645, "Leptomycihs A and B, New Antifungal Antibiotics I Taxonomy of the Prducing Strain . . . and Characterization".

Hamamoto et al., *J Antibiotics*, vol. XXXVI, No. 6, Jun. 1983, pp. 640-650, "Leptomycihs A and B, New Antifungal Antibiotics II Structure Elucidatium".

*Primary Examiner*—Thomas G. Wiseman
*Assistant Examiner*—Robin L. Teskin
*Attorney, Agent, or Firm*—Mollie M. Yang

[57] ABSTRACT

A novel complex designated herein as rigolettone complex is produced by fermentation of *Streptomyces aburaviensis* strain C-38,242 (ATCC 39290). The complex and its purified bioactive components, jildamycin and mantuamycin, exhibit antitumor activity in mouse tumor systems.

6 Claims, 8 Drawing Sheets

PROTON NMR SPECTRUM OF MANTUAMYCIN

13C NMR SPECTRUM OF MANTUAMYCIN

INFRARED ABSORPTION SPECTRUM OF JILDAMYCIN

PROTON NRM SPECTRUM OF JILDAMYCIN

13C NMR SPECTRUM OF JILDAMYCIN

4,792,522

RIGOLETTONE ANTITUMOR COMPLEX

CROSS-REFERENCE TO RELATED APPLICATIONS

This is a continuation of U.S. Ser. No. 560,772, filed Dec. 12, 1983, which is a continuation-in-part of copending U.S. Ser. No. 517,866 filed July 27, 1983 both cases now abandoned.

BACKGROUND OF THE INVENTION

1. Field of the Invention

This invention relates to new antitumor fermentation products and to their reproduction and recovery.

2. Description of the Prior Art

Japanese Kokai No. 55/118499 discloses an antibiotic designated as ATS-1287 which is produced by fermentation of Streptomyces sp. No. 1287. While the properties of ATS-1287 do not appear to correlate with those of either the jildamycin or mantuamycin components of the present invention, a recent publication in *J. Antibiotics* 36 (6): 639-650 (1983) suggests that ATS-1287 may be a mixture containing jildamycin and mantuamycin. The *J. Antibiotics* reference discloses compounds ATS-1287A and B (called leptomycin A and B) which are believed to be identical to the jildamycin and mantuamycin compounds of the present invention. The leptomycins, however, are not described as having antitumor activity and the producing microorganism, i.e. Streptomyces sp. No. 1287, can be distinguished from the *Streptomyces aburaviensis* microorganism used to produce jildamycin and mantuamycin.

SUMMARY OF THE INVENTION

There is provided by the present invention a new antitumor complex designated herein as rigolettone complex, said complex being produced by cultivating a rigolettone complex-producing strain of Streptomyces aburaviensis, most preferably Streptomyces aburaviensis strain C-38,242 (ATCC 39290) or a mutant or variant thereof, in an aqueous nutrient medium containing assimilable sources of carbon and nitrogen under submerged aerobic conditions until a substantial amount of said rigolettone complex is produced by said organism in said culture medium, and subsequently recovering the complex from the culture medium. Also provided by the present invention are two major bioactive components of rigolettone complex designated herein as jildamycin and mantuamycin which may be separated and purified by conventional isolation procedures. The rigolettone complex and the purified jildamycin and mantuamycin components exhibit antitumor activity when tested in mouse leukemia tumor systems.

DETAILED DESCRIPTION

Figure 1:
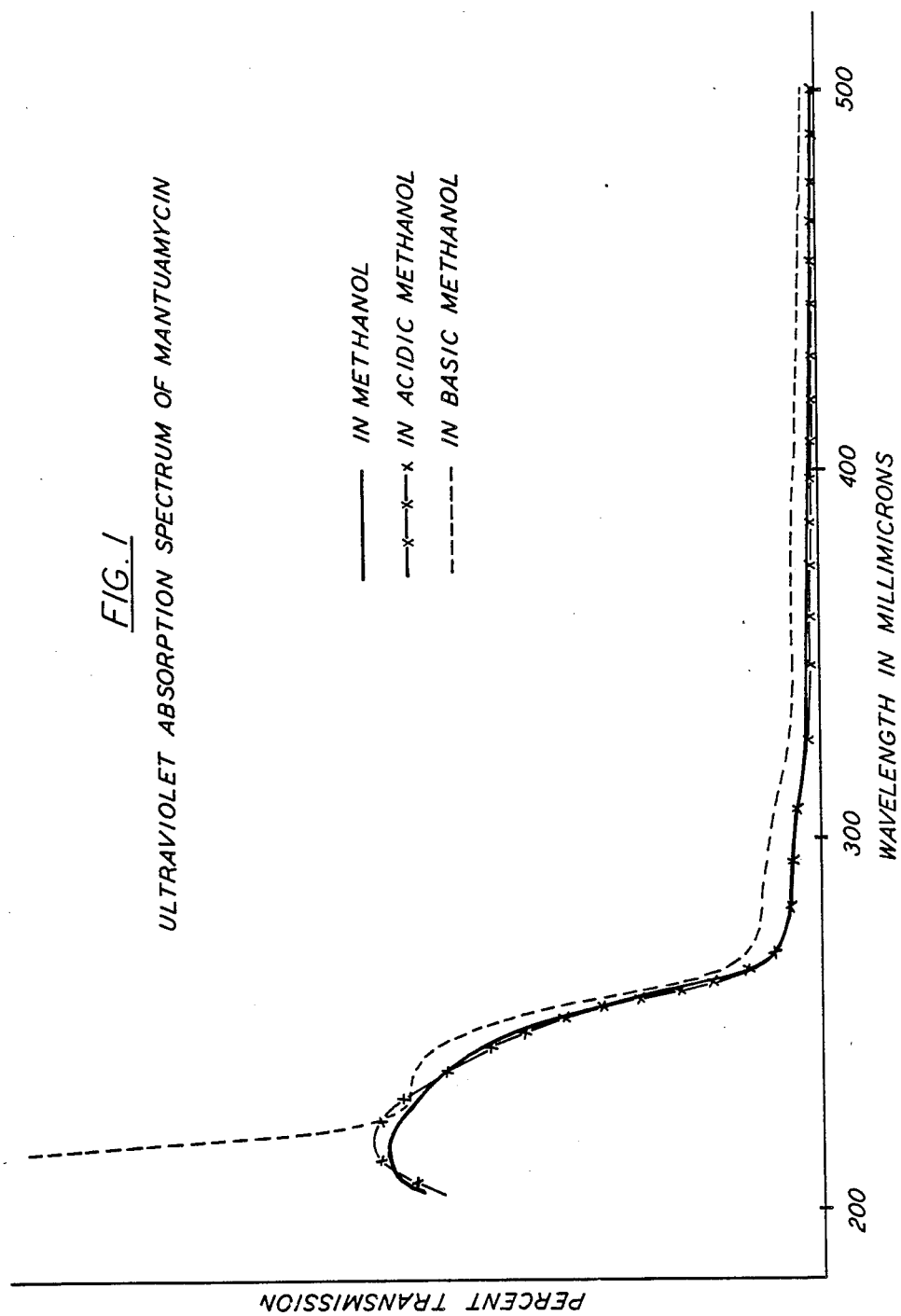
FIG. 1 shows the ultraviolet absorption spectrum of mantuamycin dissolved in methanol.

This invention relates to a novel antitumor complex designated herein as rigolettone complex and to its preparation by fermentation of a strain of Streptomyces aburaviensis designated Streptomyces aburaviensis strain C-38,242. The abovementioned organism was isolated from a soil sample collected on the campus of the University of Wisconsin, Green Bay, Wis. A biologically pure culture of strain C-38,242 has been deposited with the American Type Culture Collection, Washington, D.C., and added to its permanent collection of microorganisms as ATCC 39290.

As in the case of many fermentation product-producing cultures, fermentation of Streptomyces aburaviensis strain C-38,242 results in the production of a mixture or complex of component substances. Two major bioactive components, jildamycin and mantuamycin, have been separated from the rigolettone complex isolated from the fermentation broth.

Rigolettone complex and its purified components jildamycin and mantuamycin have been submitted to in vivo screening against mouse tumor systems and demonstrate inhibitory activity against L-1210 leukemia and P-388 leukemia. The complex and bioactive components, therefore, may be used for inhibitory mammalian tumors.

The Microorganism

The actinomycete strain No. C-38,242 was isolated from a soil sample and prepared by conventional procedures as a biologically pure culture for characterization. The results of taxonomic studies performed on strain C-38,242 indicate that the strain belongs to the genus Streptomyces and most closely resembles Streptomyces aburaviensis ATCC 23869.

Morphology

Strain C-38,242 forms aerial mycelium on substrate mycelium (0.4 μm in width). Both mycelia are long, well-branched and not fragmented into short filaments. The aerial mycelium bears spore chains monopodially or at the hyphal tip. The spore chains are long, straight or flexuous and contain 10 to 30 or more spores in a chain. Extremely short spore chains are also observed. The spores are spherical, oval, elliptical or cylindrical in shape (0.4~0.6×0.5~2.5 μm). Transmission electron microscopy indicates that the surface of the spore is smooth but often has tiny warts. Whorls, sporangia, motile spores and sclerotia are not observed.

Cultural Characteristics

Strain C-38,242 grows well in most agar media but poorly in Czapek's sucrose-nitrate agar, inorganic salts-starch agar and oat meal agar. The aerial mycelium is formed abundantly on yeast extract-malt extract agar and Bennett's agar, but is either not formed or poorly formed in most media. The color of aerial mycelium belongs to the gray color series. The reverse side of the substrate mycelium has no characteristic color. Melanoid and other distinct soluble pigments are not produced. The cultural characteristics of strain C-38,242 are shown in Table 1.

Physiological Characteristics

Maximal growth is observed at 20° C. and 28° C. The growth temperature ranges from 10° C. to 40° C. No growth is seen at 7° C. and 43° C. Melanin is not formed from L-3,4-dihydroxyphenylalanine (L-DOPA). Strain C-38,242 is tolerant to sodium chloride at 4% or less but not at 5%. The ability to utilize carbohydrates is poor, and among eleven diagnostic sugars described in Bergey's Manual, 8th ed. (1974), only D-glucose and inositol are utilized for growth. The physiological characteristics and carbohydrate utilization are shown in Tables 2 and 3, respectively.

Cell-wall Amino Acid and Whole Cell Sugar Components

The amino acid composition in cell-wall was examined according to the methods described by Becker et al. in *Appl. Microbial.* 13: 236–243 (1965) and Yamaguchi in *J. Bacteriol.* 89: 441–443 (1965). The cell-wall of strain C-38,242 contains LL-diaminopimelic acid and glycine as a diagnostic amino acid.

Taxonomy

The morphology of strain C-38,242 resembles that of the genus Pseudonocardia. Like the Pseudonocardia, strain C-38,242 forms pleomorphic spores in the long spore chain. The spores in the short chain suggest formation by budding. Zigzag-shaped hyphae are occasionally observed on the aerial mycelium. However, the cultural and physiological characteristics of strain C-38,242 and its Type I cell-wall composition indicate that strain C-38,242 is to be classified as belonging to the genus Streptomyces. According to the descriptions of Bergey's Manual, 8th ed. (1974), strain C-38,242 should be placed in the species group, RF (*Rectus flexibilis*), gray series, non-chromogenic, and smooth spore surface, which includes 17 species. Based on the species descriptions of ISP (International Streptomyces Projects) and Bergey's Manual, strain C-38,242 resembles *Streptomyces aburaviensis* in its slightly rough walled spore, poor growth in Czapek's sucrose nitrate agar and extremely limited utilization of carbohydrates. Thus, strain C-38,242 is considered to be a strain of *Streptomyces aburaviensis*.

It is to be understood that for the production of rigolettone complex and its components jildamycin and mantuamycin, the present invention, though described in detail with reference to the particular strain *Streptomyces aburaviensis* C-38,242 (ATCC 39290), is not limited to this microorganism or to microorganisms fully described by the cultural characteristics disclosed herein. It is specifically intended that the invention embrace strain C-38,242 and all natural and artificial jildamycin and/or mantuamycin-producing variants and mutants thereof.

TABLE 1

Cultural Characteristics* of Strain No. C-38,242

| Medium | | Observation |
|---|---|---|
| Tryptone-yeast extract broth (ISP No. 1) | **G: | poor: floccose, pale yellow pellets |
| | D: | none |
| Sucrose-nitrate agar (Czapek's agar) | G: | scant |
| | R: | colorless |
| | A: | none |
| | D: | none |
| Glucose-asparagine agar | G: | moderate |
| | R: | yellowish white (92)*** |
| | A: | scant |
| | D: | none |
| Glycerol-asparagine agar (ISP No. 5) | G: | abundant |
| | R: | pale yellow (89) to grayish yellow (90) |
| | A: | scant, white (263) |
| | D: | none |
| Inorganic salts-starch agar (ISP No. 4) | G: | scant |
| | R: | colorless |
| | A: | none |
| | D: | none |
| Tyrosine agar (ISP No. 7) | G: | abundant |
| | R: | grayish greenish yellow (105) to dark greenish yellow (103) |
| | A: | scant, white (263) |
| | D: | none |
| Nutrient agar | G: | abundant |
| | R: | yellowish white (92) to pale yellow (89) |
| | A: | none |
| | D: | none |
| Yeast extract-malt extract agar (ISP No. 2) | G: | abundant |
| | R: | vivid yellow (82) to strong yellow (84) |
| | A: | abundant, light gray (264) to medium gray (265) |
| | D: | moderate yellowish brown (77) |
| Oat meal agar (ISP No. 3) | G: | scant |
| | R: | colorless |
| | A: | scant, white (263) to light gray (264) |
| | D: | none |
| Bennett's agar | G: | abundant |
| | R: | grayish yellow (90) to light olive brown (94) |
| | A: | abundant, light gray (264) to medium gray (265) |
| | D: | none |
| Peptone-yeast extract-iron agar (ISP No. 6) | G: | abundant |
| | R: | pale yellow (89) |
| | A: | none |
| | D: | none |
| Colony on ISP No. 2 medium | G: | good, raised and crateriform, 3~6 mm in diameter |
| | R: | olive gray (113) |
| | A: | light gray (264) |
| | D: | none |

*observed after incubation at 28° C. for 2 to 3 weeks
**Abbreviation: G = growth; R = reverse color; A = aerial mycelium; D = diffusible pigment
***Color and number in parenthesis follow the color standard in "Kelly, K.L. & D.B. Judd: ISCC-NBS color-name charts illustrated with Centroid Color. U.S. Dept. of Comm. Cir. 553, Washington, D.C., Nov., 1975".

TABLE 2

Physiological Characteristics of Strain No. C-38,242

| Test | Response | Method or medium used |
|---|---|---|
| Range of temperature for growth | Maximal growth at 20° C. to 28° C. Moderate growth at 37° C. No growth at 7° C. and 43° C. | Bennett's agar |
| Gelatin liquefaction | Not liquefied. | 1% malt extract, 0.4% yeast extract, 0.4% glucose, 20% gelatin |
| Starch hydrolysis | Hydrolyzed. | Starch agar plate |
| Reactions in skimmed milk | Not coagulated and completely peptonized. | Difco skimmed milk |

TABLE 2-continued
Physiological Characteristics of Strain No. C-38,242

| Test | Response | Method or medium used |
| --- | --- | --- |
| Formation of melanoid pigment | Negative | Tryosine agar, peptone-yeast extract-iron agar, and tryptone-yeast extract broth |
| Tyrosinase reaction | Negative | Arai's method* |
| Nitrate reduction | Positive | Czapek's sucrose-nitrate broth. |
|  | Positive | 0.5% yeast extract, 1% glucose, 0.5% $KNO_3$, 0.1% $CaCO_3$ |
| Acid tolerance | Growth at pH 5.0. No growth at pH 4.5 | Yeast extract-malt extract agar |
| NaCl tolerance | Growth at 4% NaCl or less. No growth at 5% NaCl. | Basal medium: 1% yeast extract, 2% soluble starch, 1.5% agar |
| Lysozyme tolerance | Tolerant Growth at 0.01% lysozyme. | Trypticase soy broth plus 1.5% agar |

*Arai, T. and Y. Mikami: Chromogenicity of Streptomyces. Appl. Microbiol. 23: 402–406, 1972.

TABLE 3
Carbohydrate Utilization of Strain C-38,242

| | |
| --- | --- |
| Glycerol | + |
| D(−)-Arabinose | − |
| L(+)-Arabinose | − |
| D-Xylose | − |
| D-Ribose | − |
| L-Rhamnose | − |
| D-Glucose | + |
| D-Galactose | − |
| D-Fructose | − |
| D-Mannose | + |
| L(−)-Sorbose | − |
| Sucrose | − |
| Lactose | + |
| Cellobiose | + |
| Melibiose | − |
| Trehalose | + |
| Raffinose | − |
| D(+)-Melezitose | − |
| Soluble starch | − |
| Cellulose | − |
| Dulcitol | − |
| Inositol | + |
| D-Mannitol | − |
| D-Sorbitol | − |
| Salicin | − | observed after incubation at 28° C. for 3 weeks.
Basal medium: Pridham-Gottlieb's inorganic medium.
Abbreviation: +: positive utilization, −: negative utilization.

Fermentation

The jildamycin and mantuamycin compounds of the present invention may be prepared by cultivating a jildamycin- and/or mantuamycin-producing strain of *Streptomyces aburaviensis*, preferably *Streptomyces aburaviensis* strain C-38,242 (ATCC 39290) or a mutant or variant thereof, in a conventional aqueous nutrient medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of product, although for production of limited amounts, surface cultures and bottles may also be used. The general procedures used for the cultivation of other actinomycetes are applicable to the present invention.

The nutrient medium should contain an appropriate assimilable carbon source such as glycerol, D-glucose, D-mannose, lactose, cellobiose, trehalose or inositol. As assimilable nitrogen sources, ammonium chloride, ammonium sulfate, urea, ammonium nitrate, sodium nitrate, etc. may be used either alone or in combination with organic nitrogen sources such as peptone, meat extract, yeast extract, corn steep liquor, soybean powder, cotton seed flour, etc. There may also be added, if necessary, nutrient inorganic salts to provide sources of sodium, potassium, calcium, ammonium, phosphate, sulfate, chloride, bromide, carbonate, zinc, magnesium, manganese, cobalt, iron, and the like.

Production of the rigolettone complex can be effected at any temperature conducive to satisfactory growth of the producing organism, e.g. 10° C. to 40° C., and is conveniently carried out at a temperature of around 20° to 28° C. Ordinarily, optimum production is obtained after incubation periods of between about 8–9 days when tank fermentation is employed. If tank fermentation is to be carried out, it is desirable to produce a vegetative inoculum in a nutrient broth by inoculating a broth culture with a slant or soil culture or a lyophilized culture of the producing organism. After obtaining an active inoculum in this manner, it is transferred aseptically to the fermentation tank medium. Production of the desired products can be monitored by high performance liquid chromatography (HPLC).

Isolation and Purification

When fermentation is complete the rigolettone complex may be obtained from the fermentation broth by conventional isolation procedures, e.g. solvent extraction. Thus, the active components jildamycin and mantuamycin in the form of a mixture, i.e. rigolettone complex, may be extracted from the whole broth with a suitable organic solvent such as ethyl acetate. Oily contaminants may be removed from the crude mixture of active components by adsorbing the latter on filter aid and washing with an aliphatic hydrocarbon solvent such as Skellysolve B or hexane. The crude complex may then be eluted with acetonitrile. A toxic but tumor inactive protein impurity may be removed by dilution of a methanolic solution of the defatted complex with water to form a 65% alcohol solution. The suspended protein can be deposited as a pellet by low speed centrifugation. Removal of the protein impurity at this stage greatly simplifies the chromatographic separation steps which follow.

The rigolettone complex recovered above contains the two bioactive components jildamycin and mantuamycin which may be separated and purified in the form of colorless glasses by a series of preparative high performance liquid chromatography steps on reverse phase medium. Preferred HPLC procedures are described in detail in the examples which follow.

Physico-Chemical Properties of Jildamycin and Mantuamycin

Jildamycin and mantuamycin may be characterized by the following physico-chemical properties:

Jildamycin

Figure 5:
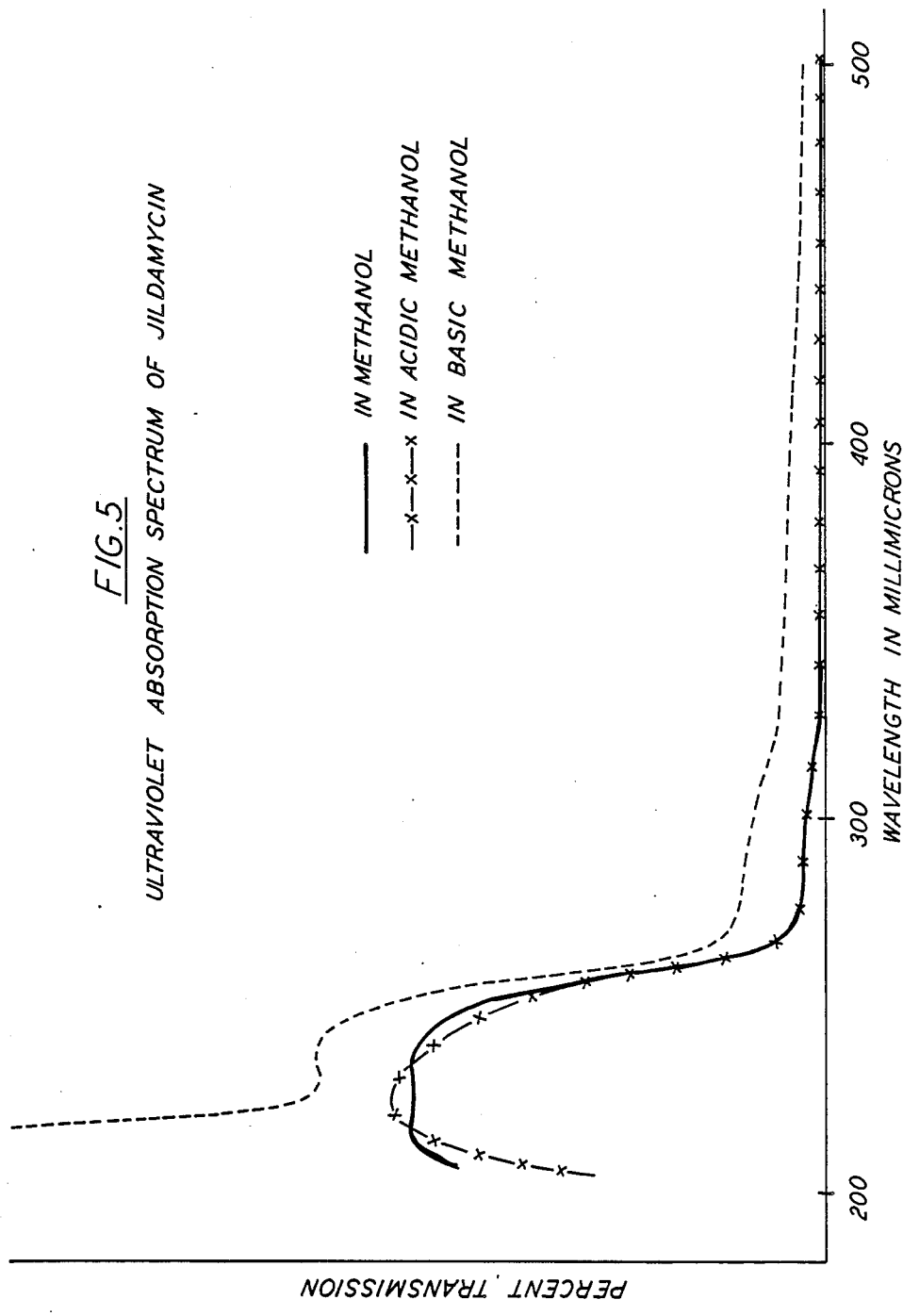
FIG. 5 shows the ultraviolet absorption spectrum of jildamycin dissolved in methanol.
Figure 6:
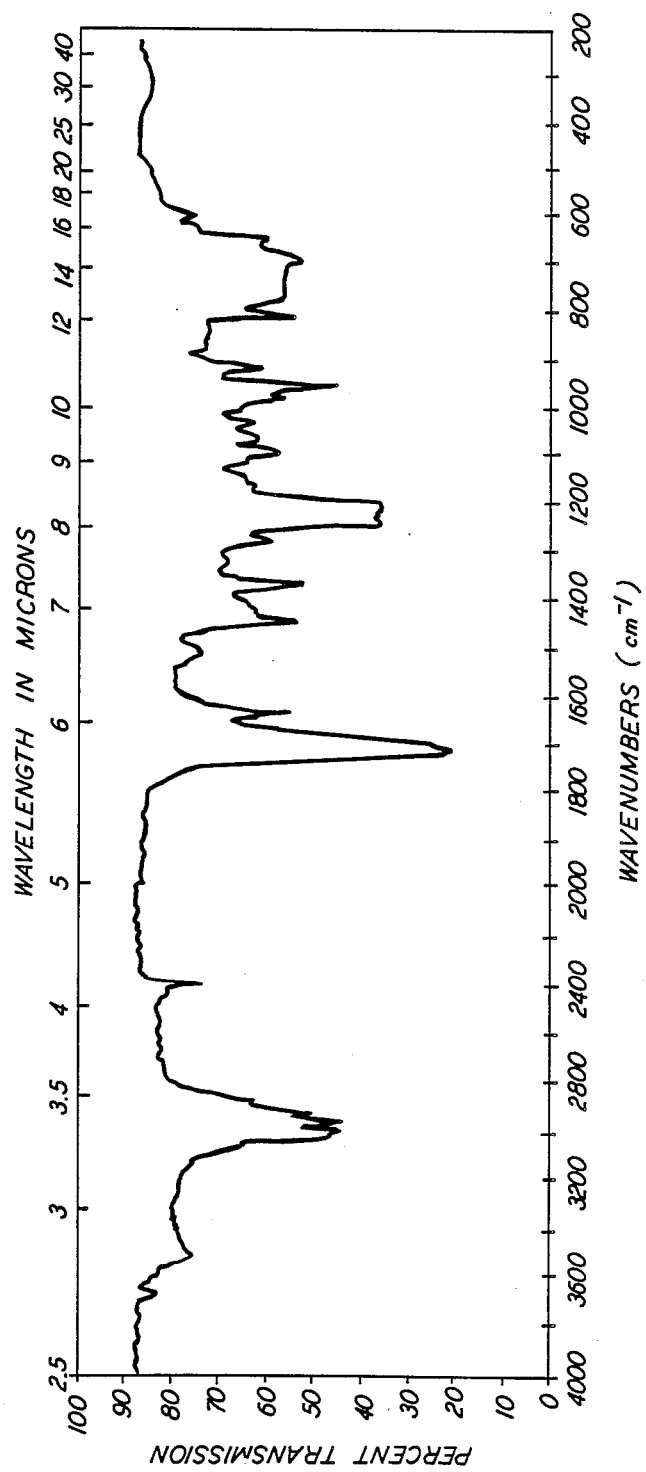
FIG. 6 shows the infrared absorption spectrum of jildamycin dissolved in $CHCl_3$.

1. The infrared absorption spectrum of jildamycin dissolved in $CHCl_3$ is shown in FIG. 6.
2. The ultraviolet absorption spectrum of a methanolic solution containing 0.01111 g jildamycin per liter of methanol is shown in FIG. 5 under neutral, acid and basic conditions.

Jildamycin differs from mantuamycin by having one less methylene group as shown by its PMR spectrum. Both compounds have two vinylogous alkyl groups as shown by their PMR spectra. For jildamycin these are both methyl groups appearing as three proton singlets at 1.82 and 1.84 ppm. For mantuamycin they are one methyl group, seen as a three proton singlet at 1.82 ppm, and an ethyl group as evidenced by a two proton quartet at 2.24 ppm and a three proton triplet at 1.05 ppm.

Based on the above-described properties, the structures of jildamycin and mantuamycin have been found to be those shown below:

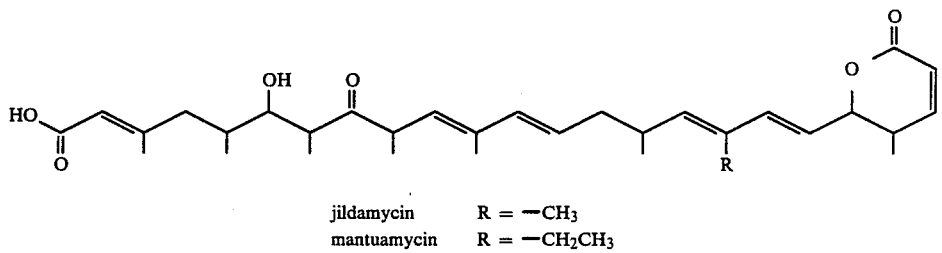

jildamycin     R = —$CH_3$
mantuamycin    R = —$CH_2CH_3$

Figure 7:
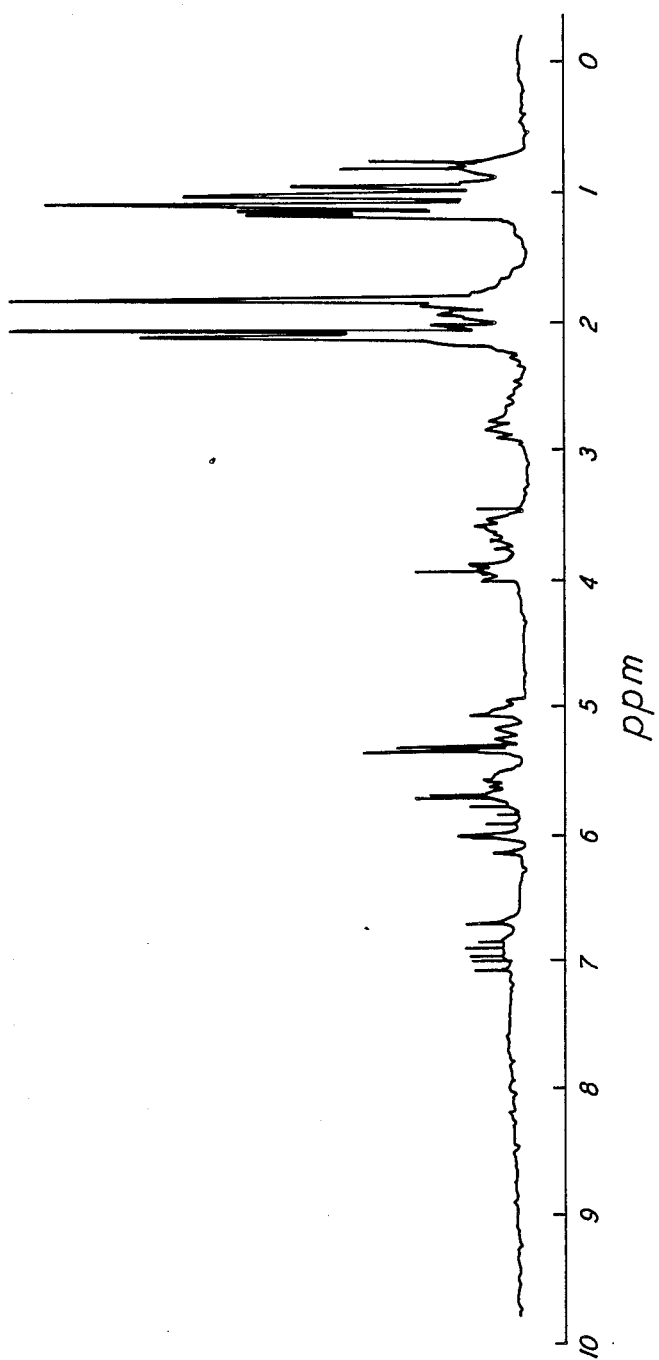
FIG. 7 shows the proton NMR spectrum of jildamycin dissolved in $CD_2Cl_2$.
Figure 8:
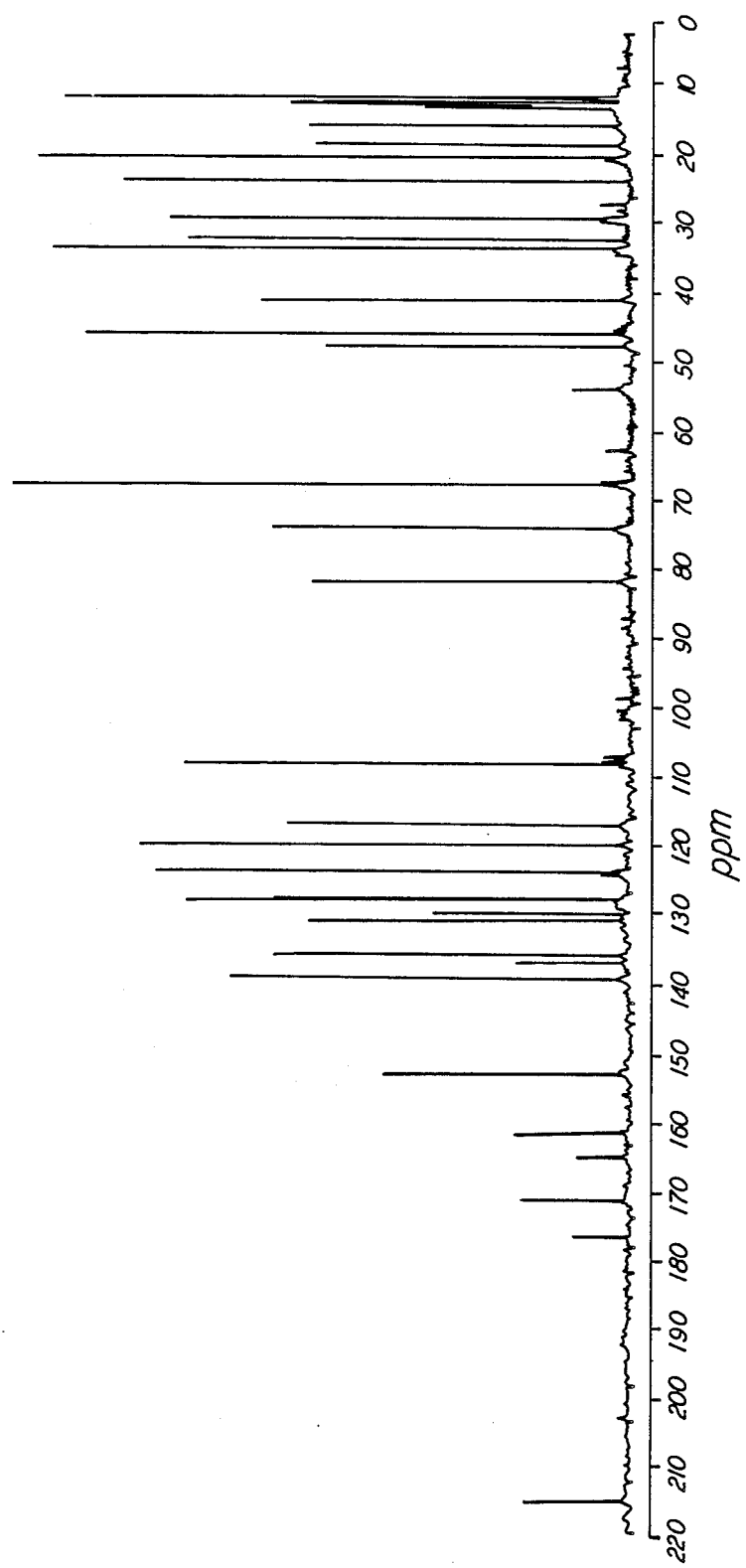
FIG. 8 shows the $^{13}C$ NMR spectrum of jildamycin dissolved in $CD_2Cl_2$.

3. The proton NMR spectrum of jildamycin dissolved in $CD_2Cl_2$ (100 MHz) is shown in FIG. 7.
4. The $^{13}C$ NMR spectrum of jildamycin dissolved in $CD_2Cl_2$ (25 MHz) is shown in FIG. 8.
5. By thin layer chromatography on $C_{18}$ reversed phase plates using a 3:2:2 (v/v) methanol:tetrahydrofuran:0.875M ammonium acetate in water solvent system, jildamycin shows a characteristic Rf of 0.40.

Mantuamycin

Figure 2:
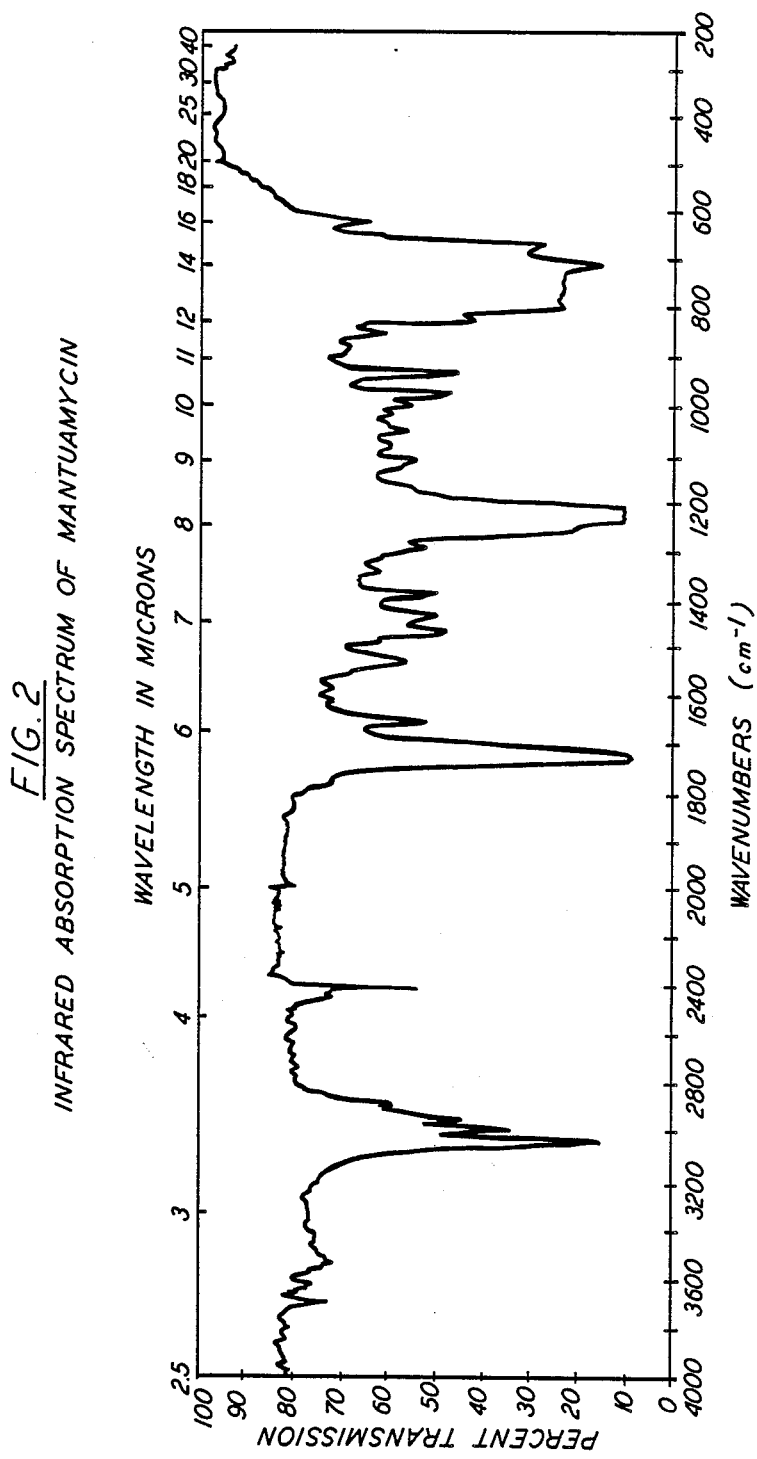
FIG. 2 shows the infrared absorption spectrum of mantuamycin dissolved in $CHCl_3$.
Figure 3:
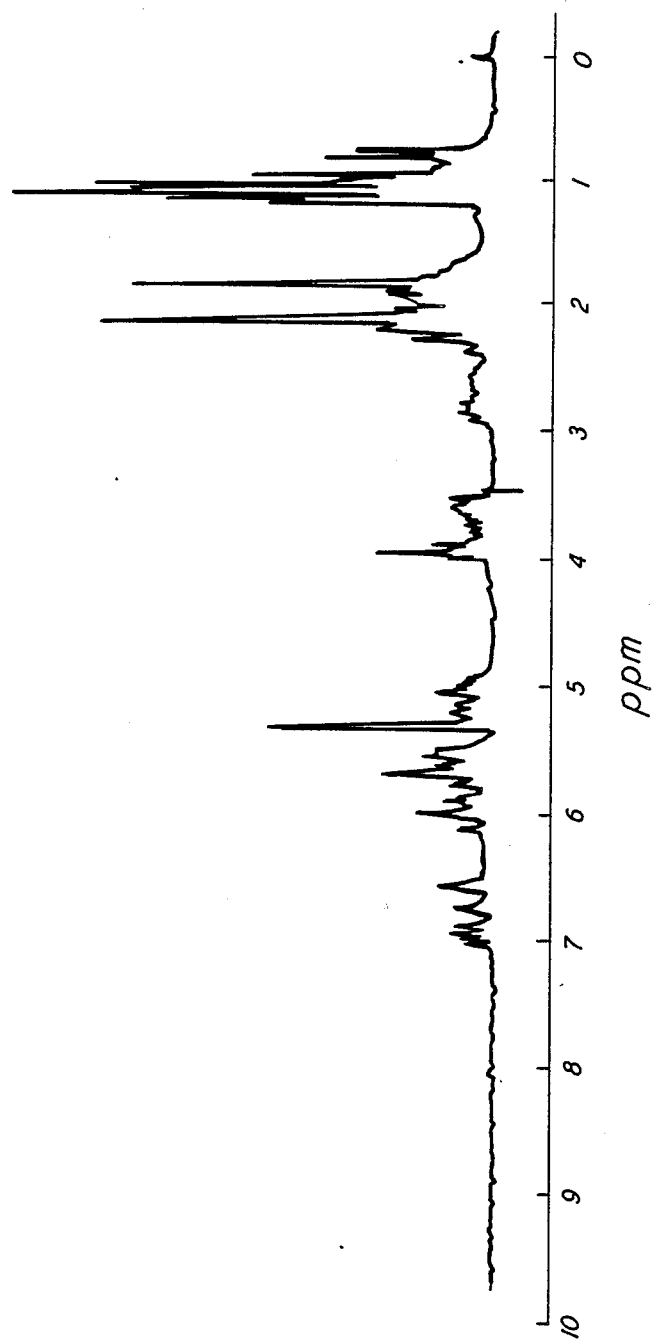
FIG. 3 shows the proton NMR spectrum of mantuamycin dissolved in $CD_2Cl_2$.
Figure 4:
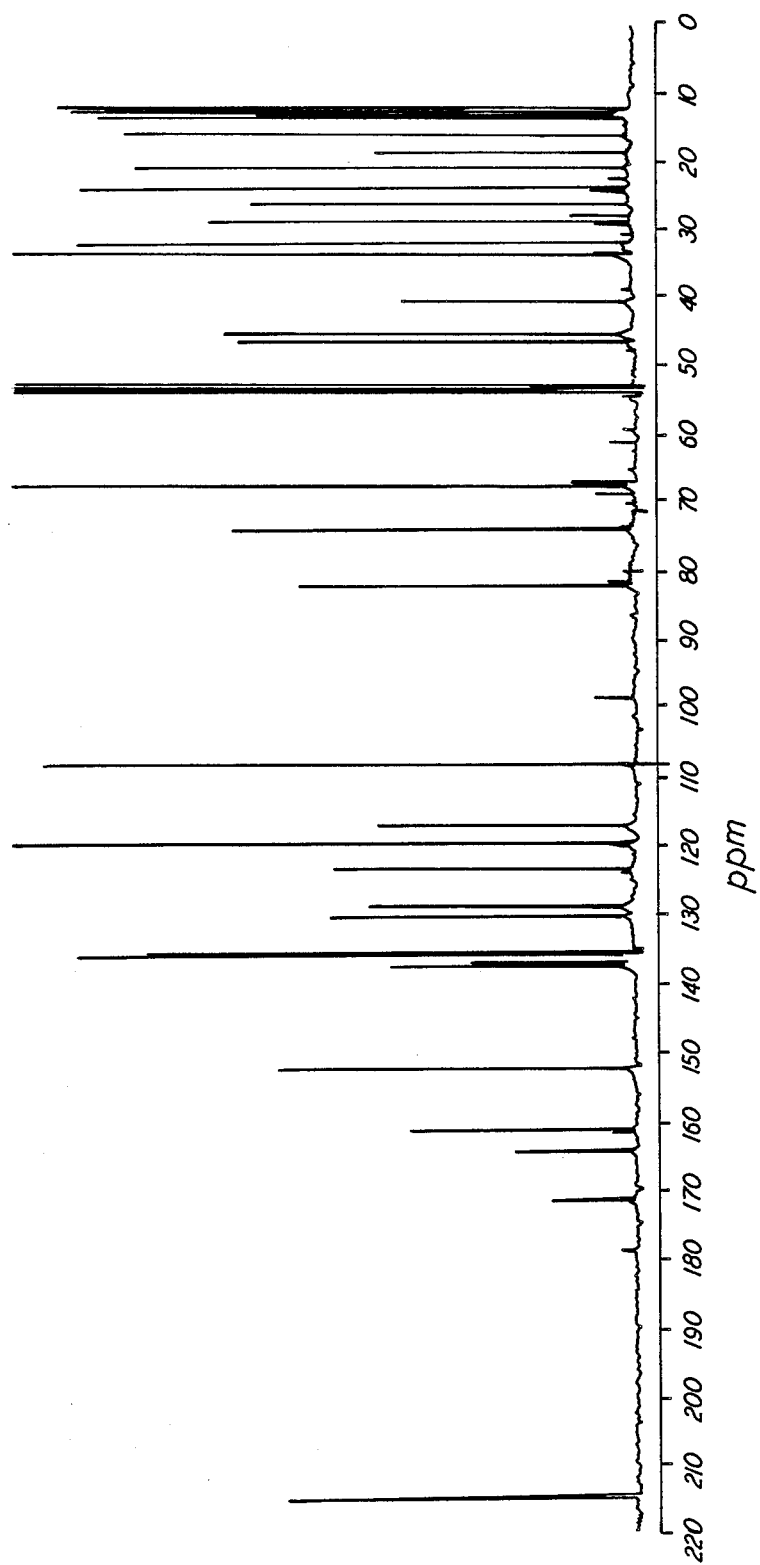
FIG. 4 shows the $^{13}C$ NMR spectrum of mantuamycin dissolved in $CD_2Cl_2$.

1. The infrared absorption spectrum of mantuamycin dissolved in $CHCl_3$ is shown in FIG. 2.
2. The ultraviolet absorption spectrum of a methanolic solution of mantuamycin containing 0.010449 g mantuamycin per liter of methanol is shown in FIG. 1 under neutral, acid and basic conditions.
3. The proton NMR spectrum of mantuamycin dissolved in $CD_2Cl_2$ (100 MHz) is shown in FIG. 3.
4. The $^{13}C$ NMR spectrum of mantuamycin dissolved in $CD_2Cl_2$ (25 MHz) is shown in FIG. 4.
5. By thin layer chromatography on $C_{18}$ reversed phase plates using a 3:2:2 (v/v) methanol:tetrahydrofuran:0.875M ammonium acetate in water solvent system, mantuamycin shows a characteristic Rf of 0.35.

Biological Properties of Jildamycin and Mantuamycin

The antitumor activities of jildamycin and mantuamycin were determined against P-388 leukemia in the mouse and the antitumor activity of mantuamycin was determined against L-1210 mouse leukemia. Lymphocytic leukemia P-388 and lymphoid leukemia L-1210 were implanted intraperitoneally into female $CDF_1$ mice at an inoculum size of $10^6$ cells per mouse. Graded doses of test compounds were administered to the mice intraperitoneally one day after tumor inoculation. In the case of the P-388 leukemia test, treatments were given once on the first day only, on days 1, 5 and 9 (q4d×3) and once daily for five days. In the L-1210 leukemia test, compound was administered once a day for five consecutive days.

Jildamycin and mantuamycin were dissolved in buffered saline solution containing dimethyl sulfoxide, and olivomycin A employed as a reference compound was dissolved in buffered saline solution. Death or survival of the treated and non-treated mice was recorded daily, and the median survival time (MST) was calculated for each of the test (T) and control (C) groups. A T/C value equal to or greater than 125% indicates that a significant antitumor effect was achieved. The results of the tests are shown in Tables 4 and 5 below.

TABLE 4

Effect of Jildamycin and Mantuamycin on P-388 Leukemia (Day 1 Treatment)

| | Dose, ip. (mg/kg/day*) | Treatment Schedule | MST (days) | T/C (%) | Average wgt. change on day 6 (g) | Survivors on day 5/ Total mice |
|---|---|---|---|---|---|---|
| Mantuamycin | .08 | gd × 5 | 12.0 | 150 | −1.2 | 6/6 |
| | .04 | | 12.0 | 150 | −2.1 | 6/6 |
| | .02 | | 10.5 | 131 | −0.9 | 6/6 |
| | .01 | | 9.0 | 113 | 0.9 | 6/6 |
| | .005 | | 9.5 | 119 | 0.8 | 6/6 |
| | .0025 | | 9.0 | 113 | 1.8 | 6/6 |
| | 0.32 | q4d × 3 | 10.5 | 131 | −2.0 | 6/6 |
| | 0.16 | | 10.0 | 125 | −0.6 | 6/6 |
| | 0.08 | | 9.5 | 119 | 0.3 | 6/6 |
| | 0.04 | | 9.5 | 119 | 0.7 | 6/6 |
| | 0.02 | | 9.5 | 119 | 1.8 | 6/6 |
| | 0.01 | | 9.5 | 119 | 2.2 | 6/6 |

TABLE 4-continued
Effect of Jildamycin and Mantuamycin on P-388 Leukemia
(Day 1 Treatment)

|  | Dose, ip. (mg/kg/day*) | Treatment Schedule | MST (days) | T/C (%) | Average wgt. change on day 6 (g) | Survivors on day 5/ Total mice |
|---|---|---|---|---|---|---|
|  | 0.64 | qd × 1 | 11.0 | 138 | −1.7 | 5/6 |
|  | 0.32 |  | 10.0 | 125 | −0.1 | 6/6 |
|  | 0.16 |  | 10.0 | 125 | 0.3 | 6/6 |
|  | 0.08 |  | 10.0 | 125 | 0.2 | 6/6 |
|  | 0.04 |  | 10.0 | 125 | 1.2 | 6/6 |
|  | 0.02 |  | 10.0 | 125 | 2.0 | 6/6 |
| Jildamycin | 0.08 | qd × 5 | 9.0 | 113 | 1.1 | 6/6 |
|  | 0.04 |  | 9.0 | 113 | 1.8 | 6/6 |
|  | 0.02 |  | 8.5 | 106 | 1.5 | 6/6 |
|  | 0.01 |  | 8.5 | 106 | 2.3 | 6/6 |
|  | 0.005 |  | 8.5 | 106 | 2.5 | 6/6 |
|  | 0.0025 |  | 8.5 | 106 | 2.1 | 6/6 |
|  | 0.32 | q4d × 3 | 9.0 | 113 | 1.1 | 6/6 |
|  | 0.16 |  | 9.0 | 113 | 1.9 | 6/6 |
|  | 0.08 |  | 9.0 | 113 | 2.1 | 6/6 |
|  | 0.04 |  | 9.0 | 113 | 2.5 | 6/6 |
|  | 0.02 |  | 10.5 | 131 | 2.3 | 6/6 |
|  | 0.01 |  | 11.0 | 138 | 1.5 | 6/6 |
|  | 0.64 | qd × 1 | 9.0 | 113 | 1.8 | 6/6 |
|  | 0.32 |  | 9.0 | 113 | 1.3 | 6/6 |
|  | 0.16 |  | 8.0 | 100 | 1.3 | 6/6 |
|  | 0.08 |  | 9.0 | 113 | 2.3 | 6/6 |
|  | 0.04 |  | 9.0 | 113 | 2.8 | 6/6 |
|  | 0.02 |  | 8.5 | 106 | 2.8 | 6/6 |
| Control = buffered saline | 0.5 ml | qd × 5 | 8.0 | 100 | 2.2 | 10/10 |
| Olivomycin A | 0.8 | q4d × 3 | 11.0 | 138 | −0.2 | 6/6 |
|  | 0.4 |  | 10.5 | 131 | 1.7 | 6/6 |

*day 1, i.p.

TABLE 5
Effect of Mantuamycin on L-1210 Leukemia
(Day 1 Treatment)

|  | Dose, ip (mg/kg/day*) | Treatment Schedule | MST (days) | T/C (%) | Average wgt. change on day 6 (g) | Survivors on day 5/ Total mice |
|---|---|---|---|---|---|---|
| Mantuamycin | 0.32 | qd × 5 | TOX | TOX | −2.4 | 1/6 |
|  | 0.16 |  | TOX | TOX | −2.3 | 3/6 |
|  | 0.08 |  | 6.0 | 86 | −2.0 | 4/6 |
|  | 0.04 |  | 9.0 | 129 | −0.9 | 5/6 |
|  | 0.02 |  | 8.0 | 114 | −1.1 | 6/6 |
|  | 0.01 |  | 8.0 | 114 | 0.2 | 5/6 |
| Control = saline | 0.5 ml | qd × 5 | 7.0 | 100 | 0.6 | 10/10 |

As shown above jildamycin and mantuamycin inhibit the growth of mouse tumor systems and are thus therapeutically useful in inhibiting the growth of mammalian tumors.

The present invention, therefore, provides a method for therapeutically treating an animal host affected by a malignant tumor which comprises administering to said host an effective tumor-inhibiting dose of mantuamycin or jildamycin or a mixture thereof.

In another aspect the present invention provides a pharmaceutical composition which comprises an effective tumor-inhibiting amount of mantuamycin or jildamycin, or a mixture thereof, in combination with an inert pharmaceutically acceptable carrier or diluent. These compositions may be made up in any pharmaceutical form appropriate for parenteral administration.

Preparations for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of mantuamycin or jildamycin used will vary according to the particular compound, the particular formulation, the mode of application and the particular situs, host and disease being treated. Many factors that modify the action of the drug will be taken into account by those skilled in the art, for example, age, body weight, sex, diet, time of administration, route of administration, rate of excretion, condition of the host, drug combinations, reaction sensitivities and severity of the disease. Administration can be carried out continuously or periodically within the maximum tolerated dose. Optimal application rates for a given set of conditions can be ascertained by those skilled in the art using conventional dosage determination tests in view of the above guidelines.

The following examples are provided for illustrative purposes only and are not intended to limit the scope of the inventin.

EXAMPLE 1

Fermentation of Rigolettone Complex

*Streptomyces aburaviensis* strain C-38,242 was maintained and transferred in culture tubes or agar slants of yeast-malt extract agar. This medium consists of 4.0 g glucose, 4.0 g yeast extract, 10.0 g malt extract and 20 g agar made up to one liter with deionized water. With each transfer the agar slant culture was incubated at 27° C. for seven days. To prepare an inoculum for the production phase the surface growth from the slant culture was transferred to a 500 ml Erlenmeyer flask containing 100 ml of sterile medium consisting of 30 g glucose, 10 g soy flour, 10 g cottonseed embryo meal and 3 g $CaCO_3$ made up to one liter with deionized water. This vegetative culture was incubated at 27° C. for 48 hours on a Gyrotary tier shaker (Model G53, New Brunswick Scientific Co., Inc.), set at 210 rev/min describing a circle with a 5.1 cm diameter. Four ml of vegetative culture was transferred to a 500 ml Erlenmeyer flask containing 100 ml of sterile production medium consisting of 20 g glucose, 20 g glycerol, 10 g soy flour, 10 g cottonseed embryo meal, 1 g $(NH_4)_2SO_4$ and 10 g $CaCO_3$ made up to one liter with deionized water. The production culture was incubated at 27° C. on the same type of shaker set at 230 rev/min. Peak yield of the desired products was after 215 hours.

For a tank fermentation 2 liters of vegetative culture was transferred to a vessel containing 30 liters of the previously described production medium. The incubation temperature was maintained at 26.5° C. The air flow rate was 70 liters/min. The agitation rate was 375 rev/min and the back pressure was 1 atmosphere. The peak of production of the desired products was at 204 hours based on HPLC analysis.

EXAMPLE 2

Isolation of Rigolettone Complex

A 30 liter batch of whole broth obtained by fermentation of *Streptomyces aburaviensis* strain C-38,242 was stirred with 20 liters of ethyl acetate for 30 min. The mixture was then admixed with 2.5–3.0 kg of diatomaceous earth and filtered on a mat of the same material. The mat was washed with another 15–20 liters of ethyl acetate and discarded. The organic and aqueous phases of the filtrate were separated and the latter discarded as well. The organic layer was filtered through fluted paper and concentrated in vacuo to an oily residue.

The residue was dissolved in methylene chloride and mixed with 100 g diatomaceous earth filter aid. The dissolved crude extract was coated onto the filter aid by vacuum concentration on a rotary evaporator to a solid residue. This was resuspended in Skellysolve B (petroleum ether, primarily n-hexane, Skelly Oil Co.) and reevaporated as before three times to completely remove methylene chloride. The coated filter aid was reslurried in and washed by percolation with 2 liters of Skellysolve B on a Buchner funnel to elute some rigolettone complex and inactive oils. The bulk of the complex, 22.36 g, was eluted with 3–4 liters acetonitrile. Later elutions with methylene chloride and methanol produced only more polar by-products.

EXAMPLE 3

Removal of Protein Impurity from Rigolettone Complex

The crude rigolettone complex obtained as in Example 2 was dissolved in methanol and water was then added to 35%. A gel formed which was readily separated by low speed centrifugation from the supernatant. The complex remained dissolved whereas material, characterized as a peptide by its pmr spectrum, was removed in the pellet. This protein impurity was found to be toxic but antitumor inactive.

EXAMPLE 4

Separation of Rigolettone Complex into Purified Mantuamycin and Jildamycin Components Preliminary resolution of crude rigolettone complex by preparative HPLC.

Crude rigolettone complex, 11.0 g, was chromatograped in two portions on a Partisil M9 10/50 ODS-3 (Whatman Chemical Separation Inc., Clifton, N.J.) column using 3:1 1% acetic acid in methanol:$H_2O$ system (system A). After removal of the peptide, samples could be injected directly onto the column. Otherwise the sample was coated onto 20 g $C_{18}$-bonded silica by evaporation from methanol solution in a rotary evaporator and the solids were packed into a large precolumn. Eight cuts of 20 ml each were taken starting at the front followed by 10 ml cuts as peaks eluted and 20 ml cuts through troughs between peaks and at the end. Cuts were assayed by thin-layer chromatography on Whatman KCl8F reversed phase plates with a 3:2:2 (v/v) methanol:tetrahydrofuran:0.875M $NH_4OAc$ pH 9 in $H_2O$ system and pooled into fractions accordingly.

A fraction enriched in jildamycin and mantuamycin from the first chromatography was rechromatographed in system A. The jildamycin/mantuamycin rich fraction from this run was now chromatographed in the same manner as above using a 7:3 (v/v) 1% acetic acid in methanol:water system (system B). This system was used for subsequent chromatographies. Jildamycin rich fractions and mixed fractions were rechromatogrammed separately. Mixed fractions from these are subjected to four additional chromatographies in sequence.

Pooled mantuamycin rich fractions from columns 2,4–9 gave 1.66 g of a yellowish glass. In addition, pooling appropriate fractions from all nine chromatographies gave 1.3 g crude jildamycin rich and 809.5 mg crude fractions containing other components of the complex.

Preparation of mantuamycin by preparative HPLC with recycle.

The mantuamycin rich fraction from the previous step (1.6 g) was dissolved in methanol, filtered and concentrated in vacuo with periodic addition of water to about 50% concentration. The solution was injected onto a Partisil M9 10/50 ODS-3 column and chromatographed using a 50:50:0.5 (v/v) THF (tetrahydrofuran)-:water:acetic acid system (System C) to remove fast and slow eluting impurities. The main peak material k′ 1.8–10.5 was now chromatographed in two portions using the same system and column with recycle (8–10 total cycles). A mantuamycin rich fraction was rechromatographed in the same system with eight cycles. Later eluting mantuamycin fractions contaminated only with slower eluting (by analytical HPLC and TLC)

impurities were pooled as were earlier eluting jildamycin fractions. The mantuamycin rich fraction was chromatographed without recycle on the same column using a 42:58:0.5 (v/v) THF:water:acetic acid system (system D) to remove the remaining jildamycin and other early eluting materials. All the mantuamycin fractions from the above were now combined and chromatographed two times in sequence using system D and recycle (3 cycles in total) to give mantuamycin, 571.5 mg, as a colorless glass. In the 3:2:2 (v/v) methanol:tetrahydrofuran:0.875M NH$_4$OAc in H$_2$O thin layer chromatography system on Whatman KC 18F C$_{18}$ reverse phase plates, mantuamycin displayed an Rf of 0.35.

Preparation of jildamycin by preparative HPLC with recycle.

The pooled jildamycin rich fractions, 1.3 g, from the chromatographies described above were chromatographed on the same column with system D as described in the previous step. The jildamycin rich cut from this column was then chromatographed three times in sequence on the same column in series with a 25 cm Partisil M9 10/25 ODS-3 column (effective bed length 75 cm) again with system D. Recycle with a total of four cycles was used in all but the first chromatography with pooling of the purified jildamycin produced. The final yield of jildamycin, as a colorless glass, was 1.02 g. In the 3:2:2 methanol:tetrahydrofuran:0.875M NH$_4$OAc in H$_2$O thin layer chromatography system on Whatman KC 18F C$_{18}$ reversed phase plates, jildamycin displayed an Rf of 0.40.

We claim:

1. The compound jildamycin having the formula

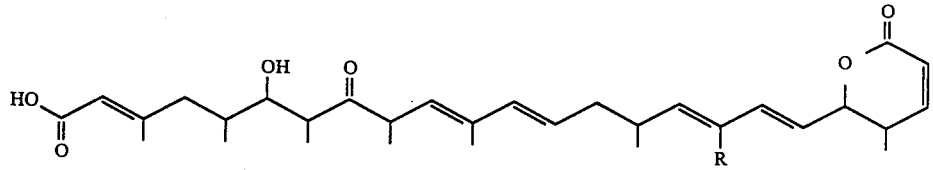

wherein R is —CH$_3$.

2. The compound mantuamycin having the formula

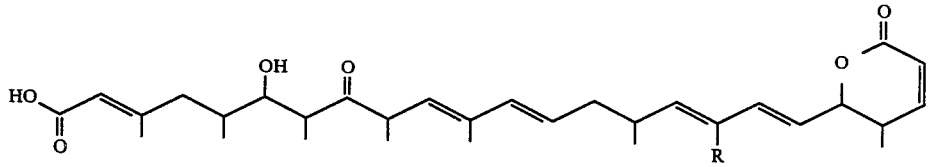

wherein R is —CH$_2$CH$_3$.

3. The process for the production of the compound jildamycin which comprises cultivating a jildamycin-producing strain of *Streptomyces aburaviensis* in an aqueous nutrient medium containing assimilable sources of carbon and nitrogen under submerged aerobic conditions until a substantial amount of jildamycin is produced by said organism in said culture medium and then recovering said jildamycin from the culture medium substantially free of coproduced substances.

4. The process according to claim 3 wherein the jildamycin-producing strain has the identifying characteristics of *Streptomyces aburaviensis* strain C-38,242 (ATCC 39290).

5. The process for the production of the compound mantuamycin which comprises cultivating a mantuamycin-producing strain of *Streptomyces aburaviensis* in an aqueous nutrient medium containing assimilable sources of carbon and nitrogen under submerged aerobic conditions until a substantial amount of mantuamycin is produced by said organism in said culture medium and then recovering said mantuamycin from the culture medium substantially free of co-produced substances.

6. The process according to claim 5 wherein the mantuamycin-producing strain has the identifying characteristics of *Streptomyces aburaviensis* strain C-38,242 (ATCC 39290).

* * * * *